United States Patent [19]
Yafuso et al.

[11] Patent Number: 5,081,042
[45] Date of Patent: Jan. 14, 1992

[54] IONIC COMPONENT SENSOR AND METHOD FOR MAKING AND USING SAME

[75] Inventors: Masao Yafuso, El Toro; Chong F. Yan, Irvine, both of Calif.

[73] Assignee: Minnesota Mining and Manufacturing Company, St. Paul, Minn.

[21] Appl. No.: 496,561

[22] Filed: Mar. 20, 1990

[51] Int. Cl.⁵ .................. G01N 21/27; G01N 31/22
[52] U.S. Cl. ............................ 436/68; 365/402; 422/57; 422/58; 422/82.06; 422/82.07; 422/82.08; 427/2; 436/172
[58] Field of Search ........... 422/82.06, 82.07, 82.08, 422/57, 58; 436/68, 172; 350/96.3, 96.33; 427/2; 356/39, 402, 410; 128/634; 385/12

[56] References Cited

U.S. PATENT DOCUMENTS

| | | | |
|---|---|---|---|
| Re. 31,879 | 5/1985 | Lubbers et al. ............. | 436/133 |
| 3,449,080 | 5/1969 | Edwards . | |
| 3,865,548 | 2/1975 | Padawer . | |
| 3,904,373 | 9/1975 | Harper . | |
| 4,194,877 | 3/1980 | Peterson . | |
| 4,321,057 | 3/1982 | Buckles ..................... | 422/58 X |
| 4,543,335 | 9/1985 | Sommer et al. ............. | 436/69 |
| 4,548,907 | 10/1985 | Seitz et al. ................. | 436/163 |
| 4,557,900 | 12/1985 | Heitzmann .................. | 422/55 |
| 4,568,518 | 2/1986 | Wolfbeis et al. ............ | 422/56 |
| 4,577,309 | 3/1986 | Hirschfeld .................. | 250/461.1 |
| 4,600,310 | 7/1986 | Cramp et al. ............... | 356/432 |
| 4,637,978 | 1/1987 | Dappen ....................... | 435/11 |
| 4,640,820 | 2/1987 | Cooper . | |
| 4,775,514 | 10/1988 | Barnikol et al. . | |
| 4,801,551 | 1/1989 | Byers et al. ................. | 436/133 |
| 4,824,789 | 4/1989 | Yafuso et al. ............... | 436/68 |
| 4,833,091 | 5/1989 | Leader et al. ............... | 436/133 |
| 4,851,195 | 7/1989 | Matthews et al. . | |
| 4,919,891 | 4/1990 | Yafuso et al. ............... | 422/82.08 |
| 4,954,318 | 9/1990 | Yafuso et al. ............... | 422/82.08 |

OTHER PUBLICATIONS

Zhujun et al., Analytica Chimica Acta 160, (1984), pp. 305–309.

Primary Examiner—Jill Johnston
Attorney, Agent, or Firm—Gary L. Griswold; Walter N. Kirn; Dale E. Hulse

[57] ABSTRACT

A composition of matter useful in a sensor for sensing the concentration of an ionic component a medium is disclosed. This composition comprises a first material including a sensing component in an amount effective to provide a signal which varies as the concentration of the ionic component in the medium varies, and a first matrix material, and a second material which includes a second matrix material which is compatible with the first matrix material, and an opague agent in an amount sufficient to render the second material effectively opaque. The first material and the second material are partially intermingled. Apparatus including such composition of matter and methods for making and using such compositions of matter are also disclosed.

41 Claims, 1 Drawing Sheet

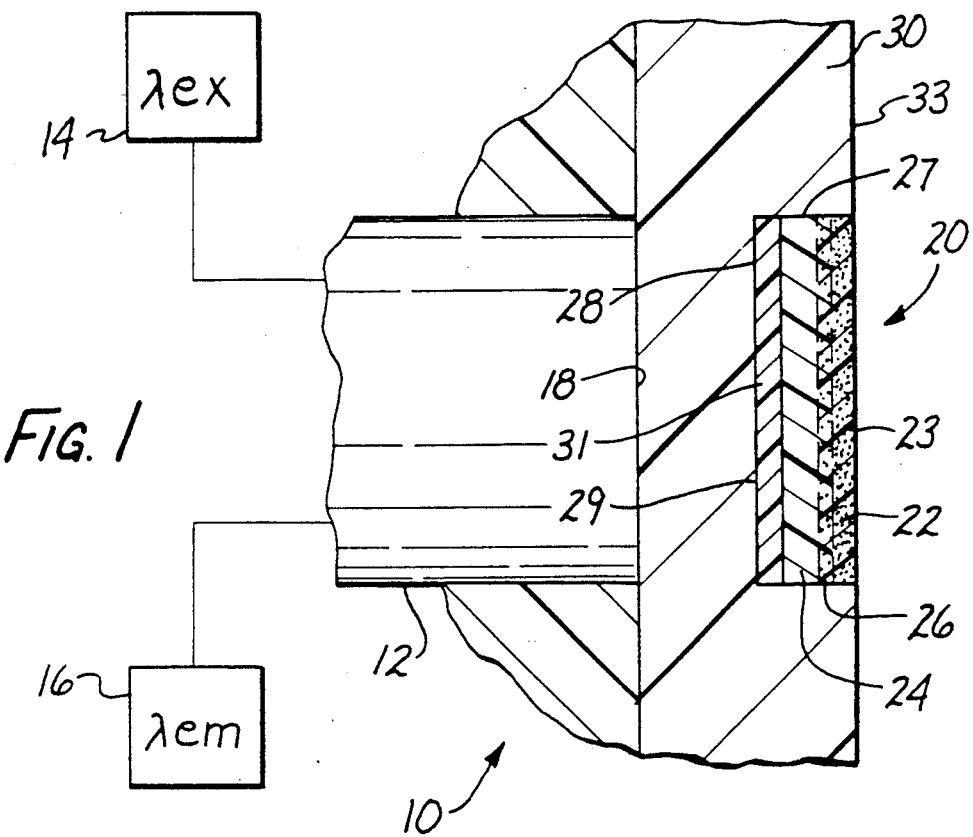
FIG. 1
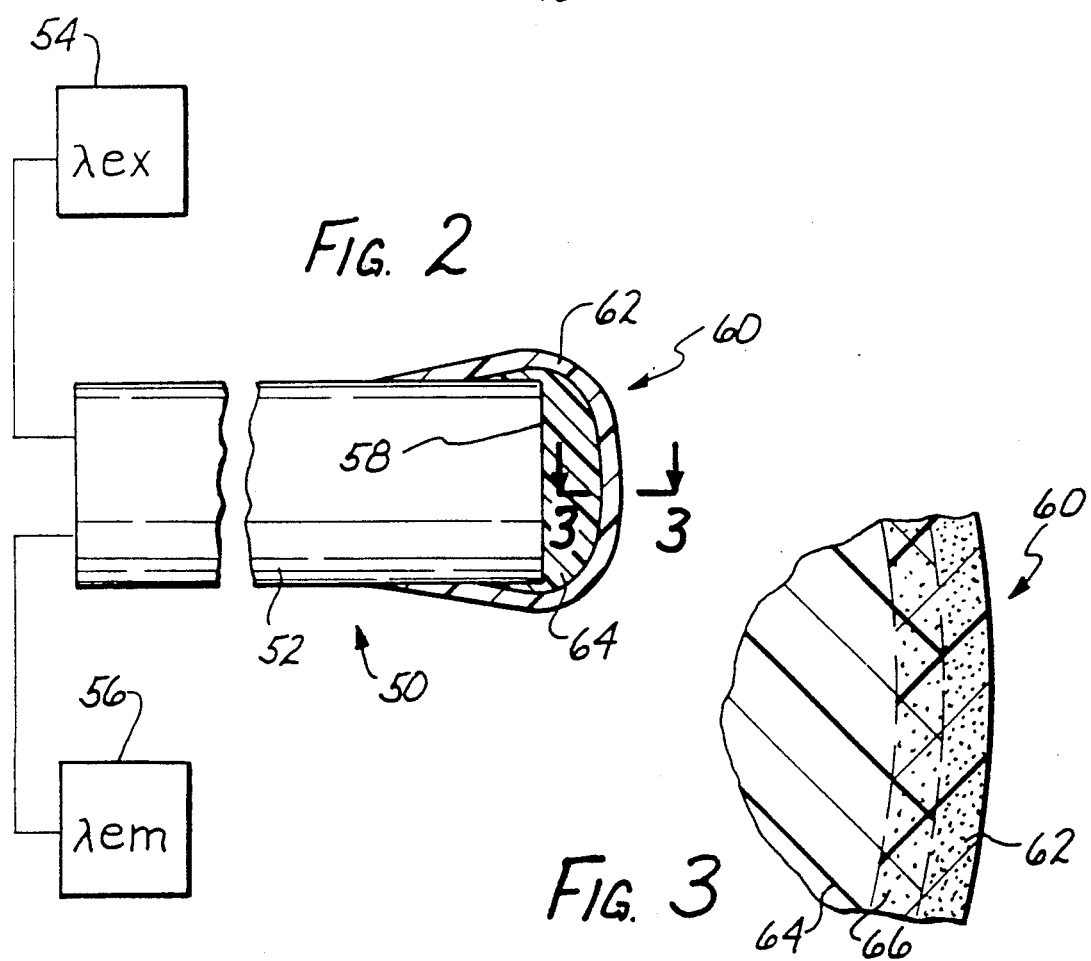
FIG. 2
FIG. 3

IONIC COMPONENT SENSOR AND METHOD FOR MAKING AND USING SAME

BACKGROUND OF THE INVENTION

This invention relates to a system for sensing ionic components. More particularly, the invention relates to sensors, and methods for making and using sensors, useful in sensing ionic components, e.g., hydrogen ions or hydroxyl ions-measured by pH, in fluids, such as blood.

It is often advantageous to determine the concentration of an ionic component in a given fluid. For example, medical diagnostic and/or treatment procedures may involve the determination of the pH value of a patient's blood or other bodily fluids. Such determinations may be made very frequently, even continuously, during the procedure.

For biological fluids, a prior known sensor uses the fluorescent properties of a dye in conjunction with the ionic permeability of a preformed integral cellulose membrane sheet. In this sensor, the cellulose membrane is chemically treated so as to introduce covalent bondable groups onto the membrane. A fluorescent dye, suitable for providing a signal which varies as the concentration of the ionic component of interest varies, is then covalently bonded to these groups to adhere the dye to the membrane. A small disc is cut from the membrane sheet and is placed in a well of a sensor cassette, which itself is placed in proximity to an optical fiber. An opaque overcoat is physically placed over the exposed surface of the disc and is secured, e.g., heat staked, to the cassette. This overcoat, which is physically separate from the disc provides optical isolation for the dye in the disc. When the dye is excited by excitation light imposed on the dye, it undergoes fluorescence, emitting a light signal. This emission light signal is transmitted, by the optical fiber, to a processor where it is analyzed to provide a determination of the concentration of the ionic component of interest.

One problem which exists with such membrane-type sensors relates to response time. Such sensors are relatively slow to respond to changes in ionic component concentration. Sensor response time is particularly important in situations where a patient's blood is frequently, or even continuously, monitored and the information obtained from such monitoring is used as a basis for treating the patient.

A faster sensor for ionic components, in particular hydrogen ions or hydroxyl ions-measured by pH, would be advantageous.

SUMMARY OF THE INVENTION

A new composition, sensor and methods for making and using the same useful in sensing the concentration of an ionic component in a medium have been discovered. The present compositions provide sensors, in particular pH sensors, which have rapid response times, and are physically stable and durable in use. These compositions are structured to have a unitary character while, at the same time, providing an acceptable sensing signal and being sufficiently optically isolated. The method of making ionic component sensors is straightforward and effective, reduces quality control problems and produces a highly reliable product. The present system takes advantage of using similar or compatible materials in different parts of the sensor. Such material compatibility allows one to produce and use a sensor which provides substantial advantages.

In one broad aspect of the present invention, a composition of matter useful in sensing the concentration of an ionic component in a medium is provided. This composition comprises a first material, preferably a first layer, including a sensing component in an amount effective to provide a signal which varies as the concentration of the ionic component of interest in the medium varies, and a first matrix material which is preferably permeable to the ionic component of interest, and preferably acts as a carrier for the sensing component. A second material, preferably a second layer, is provided and includes a second matrix material which is permeable to the ionic component of interest and is compatible with the first matrix material, and an opaque agent in an amount effective to render the second material, in particular that portion of the second material which is not intermingled with the first material, effectively opaque. The second matrix material preferably acts as, and is present in an amount effective to be, a carrier and/or binder for the opaque agent. The first material and the second material are partially intermingled, e.g., intermixed and/or interpenetrated, so that there is a substantial bond, namely, a physical or mechanical bond, between the first material and the second material. Thus, the second material, which may be considered an overcoat of the first material, is an integral part of the composition, provides the desired opacity, e.g., for optical isolation of the sensing component in the first material, and yet allows a substantial portion of the sensing component to be substantially free and clear of the opaque agent. Thus, not only is the composition structured to be stable and durable in use, but also the sensing component is able to provide an accurate and reliable signal in response to the concentration of the ionic component of interest in the medium. Importantly, the response time of this "partially intermingled" sensing composition is very good. That is, the emitted signal from the sensing composition responds rapidly to variations in the concentration of the ionic component of interest in the medium being monitored.

In another broad aspect of the invention, an apparatus useful in sensing the concentration of an ionic component in a medium is provided. This apparatus comprises a sensor means including a quantity of the sensing composition described above. In addition, the apparatus further includes signal means, e.g., one or more optical fibers, capable of transmitting a signal from the sensing component.

The above-noted composition and apparatus can be used in a method for sensing the concentration of an ionic component in a medium. This method comprises contacting the composition or sensor means of the apparatus with the medium to be monitored. The signal given off by the sensing component is analyzed, e.g., using conventional and well known techniques, to determine the concentration of the ionic component of interest in the medium.

In a further broad aspect of the present invention, a method for making a sensor useful in sensing the concentration of an ionic component in a medium is provided. This manufacturing method comprises applying a second composition to a surface, e.g., an exposed surface, of a first composition. The first composition comprises a sensing component in an amount effective to provide a signal which varies as the concentration of the ionic component in a medium varies and a first matrix material which is solid. The second composition comprises a liquid medium, an opaque agent and a second matrix material which is compatible with the first matrix material and is solubilized in the liquid medium. Preferably, a portion of the first matrix material in the first composition is solubilized in this liquid medium. A solid second matrix material is formed from the solubilized second matrix material. The sensor produced in accordance with this method has substantially all the advantages of the sensing composition described previously.

These and other aspects and advantages of the present invention are set forth in the following detailed description and claims, particularly when considered in conjunction with the accompanying drawings in which like parts bear like reference numerals.

BRIEF DESCRIPTION OF THE DRAWINGS

FIG. 1 is a schematic illustration of a sensor apparatus according to the present invention.

FIG. 2 is a schematic illustration of an alternate embodiment of a sensor apparatus according to the present invention.

FIG. 3 is a cross-sectional view taken generally along line 3—3 of FIG. 2. FIG. 3 is an enlarged view of a portion of the sensor apparatus of FIG. 2, and is included to show the intermingled or overlap zone 66. As disclosed herein, the thickness of the intermingled zone is relatively small compared to the thickness of the first zone containing the sensing component. Hence, no attempt has been made to show intermingled zone 66 in the general schematic illustration of FIG. 2; this intermingled zone 66 is instead shown in the enlarged view of FIG. 3 for purposes of clarity. It should also be noted that the thickness ratios comparing the thickness of the first zone containing the sensing component, the second zone containing the opaque agent, and the intermingled zone, are as set forth in the following description, and no attempt has been made to represent these relative thickness ratios in the drawings.

DETAILED DESCRIPTION OF THE INVENTION AND DRAWINGS

The present ionic component sensing compositions include a first material and a second material. These two materials are partially intermingled. That is, there are one or more localized zones in the compositions which include one or more components, preferably all the components, of both the first and second materials. In one embodiment, the present sensing composition comprises a first zone including at least one component, preferably all the components, of the first material, and preferably being substantially free of components of the second material; an intermediate zone, preferably located between the first and second zones, including at least one component of both first and second materials, preferably all the components of both first and second materials; and a second zone including at least one component, preferably all the components, of the second material, and preferably being substantially free of components of the first material. This intermingled, e.g., intermixed or interpenetrated, structure provides a physically stable sensing composition which is durable in use. In addition, and quite importantly, these intermingled sensing compositions are highly responsive to changes in the concentration in the ionic component of interest in the medium being monitored.

The first material, e.g., layer, of the sensing compositions includes a sensing component in an amount effective to provide a signal which varies in response to variations in the concentration of the ionic component of interest in the monitored medium, and a first matrix material which is permeable to this ionic component of interest. The second material, e.g., layer, includes a second matrix material which is compatible with the first matrix material, and an opaque agent in an amount effective to render the second material effectively, e.g., for ionic component sensing, opaque.

The signal provided by the sensing component or components in response to the presence of the ionic component in the medium varies as the concentration of the ionic component in the medium being monitored varies. Many sensing components useful to provide a concentration variable signal in response to ionic components are conventional and well known in the art and can be used in the present invention. Examples of the ionic components which can be sensed include hydrogen ions ($H^+$), hydroxyl ions ($OH^-$), metal ions, such as alkali and alkaline earth metal ions, e.g., potassium ions ($K^+$), sodium ions ($Na^+$), lithium ions ($Li^+$) and calcium ions ($Ca^{++}$), and the like.

Any suitable sensing component may be employed in the present invention provided that the sensing component has no substantial detrimental effect on the functioning of the present system or on the medium being monitored. The sensing component is preferably an optical indicator, such as an absorbance indicator or a fluorescence indicator. More preferably, the sensing component is a fluorescence indicator. The present invention is particularly useful in sensing the concentration of hydrogen ions ($H^+$) or hydroxyl ions ($OH^-$). In this embodiment, the pH of the medium is often determined. Suitable pH sensing components include many well known pH indicators and/or functionalized derivatives of such indicators. Among the useful pH sensing components are hydroxypyrene 3,6,8- trisulfonic acid (hereinafter referred to as HPTS or hydroxypyrene trisulfonic acid) and derivatives, e.g., salts, thereof, phenolphthalein, fluorescein, phenol red, cresol red, pararosaniline, magenta red, xylenol blue, bromocresol purple, bromophenol blue, bromothymol blue, metacresol purple, thymol blue, bromophenol blue, bromothymol blue, tetrabromophenol blue, brom-chlorphenol blue, bromocresol green, chlorphenol red, o-cresolphthalein, thymolphthalein, metanil yellow, diphenylamine, N, N-dimethylaniline, indigo blue, alizarin, alizarin yellow GG, alizarin yellow R, congo red, methyl red, methyl orange, orange I, orange II, nile blue A, ethyl bis (2,4-dinitrophenyl) acetate, gamma-naphthoibenzein, methyl violet 6B, 2, 5-dinitrophenol, and/or the various functionalized derivatives of the above species.

Sensing components for other ionic components can be made from organic species which include fluorescein, diiodofluorescein, dichlorofluorescin, phenosafranin, rose bengal, eosin I bluish, eosin yellowish, magneson, tartrazine, eriochrome black T and others.

The preferred pH sensing component is hydroxypyrene trisulfonic acid, derivatives of hydroxypyrene trisulfonic acid and mixtures thereof.

The amount of sensing component employed should be sufficient to provide an ionic component concentration dependent signal which is sufficient, e.g., is of sufficient intensity, to be transmitted and analyzed in determining the concentration of the ionic component of interest in the medium being monitored. The specific amount of sensing component employed varies depending, for example, on the specific sensing component being employed, the ionic component being sensed, the medium being monitored, and the other components of the sensor system being employed.

The first and/or second matrix materials useful in the present invention are permeable to the ionic component of interest, and are preferably substantially insoluble in the medium to be monitored. That is, the first and second matrix materials should be structured so that the ionic component of interest can physically permeate such matrix materials. Any suitable first and second matrix materials may be employed provided that such matrix materials have no substantial detrimental effect on the functioning of the system or on the medium being monitored.

Each of the first and second matrix materials is preferably a polymeric material. One important feature of the present invention is that the second matrix material is compatible with the first matrix material. As used herein, the term "compatible" means that the second matrix material is capable of forming a sufficiently strong bond, physically, with the first matrix material so that the second material remains secured or bonded to the first material at normal use conditions of the present composition. The first and second materials are situated so that these two materials are partially intermingled with each other. This intermingled zone provides a region where the first and second materials are bound or secured to each other. The second compatible matrix material is such as to be capable of forming this intermingled zone with the first matrix material-containing first material.

Macromolecular hydrophilic polymers which are substantially insoluble in the medium to be monitored and permeable to the ionic component of interest are particularly useful as first and/or second matrix materials, e.g., in systems used to monitor aqueous media. Such polymers include, for example, cellulosic materials, high molecular weight or cross-linked polyvinyl alcohol (i.e., PVA), polyurethanes, quaternarized polystyrenes, sulfonated polystyrenes, polyacrylamides, polyhydroxyalkyl acrylates, polyvinyl pyrrolidones, hydrophilic polyamides, polyesters and mixtures thereof. In a particularly useful embodiment, the first and second matrix materials have substantially the same chemical composition. In systems used to measure pH, cellulosic materials, and in particular cellulose, are preferred.

The matrix material polymers can be anionic or cationic in character, as desired, and can be made so using conventional and well known techniques. For example, such polymers, or functionalized derivatives thereof, may be reacted with an acidic component, such as an organic sulfonic acid, a carboxylic acid and the like, to form anionic polymers; or may be reacted with a basic component, such as an organic amine and the like, to form cationic polymers. An especially useful polymer for use in both the first and second matrix materials is substantially non-ionic cellulose.

The sensing component may be bonded, physically or chemically, to the first matrix material. Alternately, the first material may include a physical mixture containing the sensing component and first matrix material.

Chemical bonding of the sensing component to the first matrix material can be accomplished either by direct coupling of the sensing component to reactive sites on the first matrix material, as for instance, the hydroxyl groups on either cellulose or PVA, or through indirect coupling utilizing a substituent group which is coupled or chemically bound to the first matrix material. For example, alkylamines can be first joined to at least a portion of the hydroxyl groups on the cellulose backbone by forming an ether between the alkyl portion of the alkylamine and the cellulose backbone. This leaves the amino functionality of the alkylamine available for reaction with the sensing component to join the sensing component to the first matrix material.

The amount of first matrix material used may vary depending, for example, on the specific first matrix material and sensing component being employed. Such first matrix material is preferably present in an amount effective to act as a carrier for the sensing component and/or as a filler to provide additional volume or substance to the first material. Since the first matrix material is permeable to the ionic component of interest, this first matrix material facilitates interaction between this ionic component and the sensing component which results in the ionic component concentration variable signal, described herein. The sensing component is preferably substantially uniformly distributed in the first material and in the first zone when the sensing composition includes a first zone, an intermingled zone and a second zone, as described herein. In the intermingled zone, the concentration of sensing component is reduced, relative to the sensing component concentration in the first zone, since components of the second zone are also present.

Any opaque agent may be used provided that such agent or agents function to provide the desired degree of opacity, e.g., for effective optical isolation of the sensing component, and have no substantial detrimental effect on the functioning of the present system or on the medium being monitored. Among the opaque agents useful in the present invention are carbon black, other carbon based opaque agents, ferric oxide, metallic phthalocyanines and the like. Such opaque agents are preferably substantially uniformly dispersed in the second material in an amount effective to provide the desired degree of opacity, e.g., to provide the desired optical isolation. A particularly useful opaque agent is carbon black.

The amount of second matrix material used may vary depending, for example, on the specific second matrix material and opaque agent being employed. Such second matrix material preferably acts as a filler to provide additional volume or substance to the second material. The opaque agent is preferably substantially uniformly distributed in the second material, and in the second zone when the sensing composition includes a first zone, an intermingled zone and a second zone, as described herein. In the intermingled zone, the concentration of opaque agent is reduced, relative to the opaque agent concentration in the second zone, since components of the first zone are also present.

The relative amounts or sizes of the various materials or zones of the present sensing compositions may vary widely, provided that such sensing compositions function as described herein. In order to obtain highly favorable sensor response times, it is preferred that the second material, or second zone and intermingled zone, be present in a minor amount, e.g., be thin, relative to the first material, or first zone, respectively. Of course, the second material, or second zone, should have sufficient volume or thickness to provide the sensing composition with the desired opacity, e.g., optical isolation. Also, the intermingled zone should have sufficient volume or thickness to provide the sensing composition with the desired physical stability and/or durability in use. In a useful embodiment, where the pH of blood is being monitored using a hydroxypyrene trisulfonic acid sensing component, cellulose is employed as both the first and second matrix materials and carbon black as the opaque agent, the relative thickness of the first material or first zone to the second material or second zone, respectively, is preferably in the range of about 1 to 0.01 to about 1 to 0.7, while the relative thickness of the first zone to the intermingled zone is preferably in the range of about 1 to 0.005 to about 1 to 0.25.

The present compositions may, and preferably are, included in a sensor prepared as follows. A quantity of a first composition is situated so as to have an exposed surface. This first composition comprises a sensing component and a solid first matrix material, as described herein. This first composition may be situated on and/or about the optical surface of an optical fiber, or in a cavity or well having one open end in a sensor holder which is preferably substantially transparent, such as a substantially transparent sensor cassette. A second composition is applied to this exposed surface. This second composition comprises a liquid medium, an opaque agent, as described herein, and a second matrix material which is compatible with the first matrix material and is solubilized in the liquid medium. A solid second matrix material is formed from this solubilized second matrix material.

The liquid medium may be, and preferably is, aqueous-based. The liquid medium preferably includes one or more components which act to solubilize the second matrix material. When the first, and preferably second, matrix material is cellulosic, the liquid medium is preferably basic in nature, in particular a basic aqueous medium. Examples of basic components which may be used include metal hydroxides, amines, in particular organic amines, and mixtures thereof. Particularly useful results are achieved using cupric hydroxide, ethylene diamine and mixtures thereof. Other components may be included in the second composition, e.g., to provide one or more beneficial properties. For example, glycerol and the like components can be added in an amount effective to facilitate forming a substantially uniform thickness second composition coating on the exposed surface of the first composition.

A solid second matrix material is formed from the solubilized second matrix material. This forming step may involve evaporation and/or drying to remove liquid from the second matrix material. In addition, various other procedures may be used in forming the solid second matrix material. Such procedures depend on the specific solid second matrix material to be formed. For example, when the second matrix material is cellulosic in nature, the formation of the solid second matrix material preferably includes contacting the precursor of this solid material with an acid, more preferably with an acidic aqueous medium. Such acid treatment typically utilizes an acid or acids such as, for example, sulfuric acid, nitric acid, hydrochloric acid, mixtures thereof and the like. Of course, the acid or acids selected should have no substantial detrimental effect on the other components of the sensor system. When a portion of the first matrix material is solubilized, the forming step acts to form solid first matrix material from this solubilized first matrix material which solid first matrix material forms part of the intermingled zone with a portion of the solid second matrix material.

The sensing compositions of the present invention are useful in a method for sensing the concentration of an ionic component in a medium, preferably a fluid medium, and in particular blood. The medium to be monitored is contacted with the sensing composition. The sensing component in the sensing composition, preferably in the first material of the sensing composition, is caused to emit a signal which varies as the concentration of the ionic component of interest in the medium being monitored varies. For example, when a fluorescence sensing component is used, a light signal of one wavelength is directed toward the sensing component in the sensing composition. This "excitation" signal is designed to cause the sensing component to fluoresce and thereby emit a signal which is dependent on the concentration of the ionic component of interest in the medium being monitored. This "emission" signal is analyzed, e.g., using techniques which are well known in the art, to determine the concentration of the ionic component of interest in the medium being monitored.

In a particularly useful embodiment, an optical fiber is used to transmit the "emission" signal from the sensing component. More particularly, the same optical fiber is used to transmit the "excitation" signal to the sensing component and to transmit the "emission" signal from the sensing component.

The following non-limiting example illustrates certain aspects of the present invention.

EXAMPLE

A pH sensor was made as follows. 15.75 gm of $CuSO_4$ was dissolved in 150 ml of distilled water. $Cu(OH)_2$ was precipitated from this solution by slowly adding, with stirring, 13 ml of 20% by weight NaOH in water. The precipitate was collected by centrifugation, and washed with water two times. The weight of the water/precipitate cake was reduced to 41 gms by filtration. 10 gms of ethylene diamine was combined with this cake and resulted in a basic aqueous solution.

100 mg of carbon black was dispersed with vigorous stirring in 5 gms of this basic aqueous solution using a mechanical homogenizer, i.e., a Virtis 23 homogenizer. 100 mg of cotton (cellulose) was added to this dispersion and the cotton was allowed to, and did, dissolve at room temperature. After this dissolution, 375 mg of glycerol was blended into the dispersion to provide the bulk overcoat material.

A transparent cassette was provided which included a cavity or well having one open end. This cassette was made of polycarbonate material. A disc of cellulose including covalently bonded hydroxypyrene trisulfonic acid was placed in the cavity and bonded to the cassette using a polyurethane-based adhesive. A small amount of the bulk overcoat material was painted on this disc so that none of the disc was exposed through the opening of the cavity. This coating was allowed to dry for 5 minutes and then contacted with an aqueous solution containing 5% by weight of HCl and 30% by weight of glycerol for 3 minutes. The aqueous solution was then blotted off. The coating was contacted with this aqueous solution for 3 minutes and the aqueous solution was blotted off 5 more times. Afterwards, the coating was contacted twice, for 3 minutes each time, with an aqueous wash solution containing 33% by weight of glycerol.

FIG. 1 shows a pH sensor of the invention, shown generally at 10. An optical fiber 12 is connected to a light transmitting apparatus 14. The light transmitting apparatus 14 generates the excitation light. The optical fiber 12 is also connected to light receiving apparatus 16. The light receiving apparatus 16 receives and analyzes the emission light from fluorescence sensing component as described in Lubbers et al U.S. Pat. No. Re. 31,879 and Heitzman U.S. Pat. No. 4,557,900. Each of these patents is incorporated by reference in its entirety herein.

The optical surface 18 of the fiber 12 is spaced apart from the sensing composition, shown generally at 20. Sensing composition 20 is produced as described in the example herein. Sensing composition 20 includes an opaque zone 22, a sensing component zone 24 and an intermingled zone 26 located therebetween. The thickness ratio of sensing component zone 24 to intermingled zone 26 to opaque zone 22 is about 1 to 0.01 to 0.5. Sensing composition 20 is located in well 28 of cassette 30 as shown in FIG. 1 using polyurethane-based adhesive layer 31. Well 28 is open at one end, includes a right circular cylindrical side wall 27 and a circular bottom wall 29. Well 28 has a diameter of 0.15 inches and a depth of 0.0035+0.001 inches. The top surface 23 of opaque zone 22 is substantially flush with the inner surface 31 of cassette 30. Cassette 30 is made of transparent polycarbonate.

In use, the medium the pH of which is to be monitored, e.g., blood, is allowed to come into contact with sensing composition 20, e.g., by flowing this medium in cassette 30 back and forth across sensing composition 20. Excitation light of an appropriate wave length from the light transmitting apparatus 14 is fed to the optical fiber 12. This excitation light interacts with the HPTS in the sensing component zone 24 causing the HPTS to fluoresce. The emission light from the fluorescence is fed to light receiving apparatus 16 where it is processed and analyzed to determine the pH of the medium being monitored.

The present invention also has applicability to a system in which a sensing composition is placed directly on the optical surface of an optical fiber. Such a system is illustrated in FIGS. 2 and 3. In this embodiment, a sensor apparatus, shown generally at 50, includes an optical fiber 52, a light transmitting apparatus 54 and a light receiving apparatus 56. Optical fiber 52 includes an optical surface 58. In addition, a sensing composition, shown generally at 60, is included. Sensing composition 60 includes an opaque zone 62, a sensing component zone 64 and an overlap zone 66. The sensing composition 60 is located on optical fiber 52. This can be accomplished by applying a mixture containing HPTS and cellulose on and about the optical surface 58 and regenerating the cellulose using an acidic aqueous solution so as to provide the desired amount of sensing component on and about optical surface 58. A basic aqueous suspension including carbon black and solubilized cellulose, similar to that described in the example herein, can be applied to the optical fiber 52 to result in partial solubilizing of the cellulose in the previously applied mixture. The solubilized cellulose is then regenerated to form the structure shown in FIGS. 2 and 3.

In use, sensor 50 functions substantially as does sensor 10. Thus, the optical fiber 52 bearing the sensing composition 60 is placed in contact with the medium the pH of which is to be monitored. Excitation light of an appropriate wave length from the light transmitting apparatus 54 is fed to the fiber 52. This interacts with the HPTS in the sensing composition 60 causing the HPTS to fluoresce. The emission light from the fluorescence is fed to light receiving apparatus 56 where it is processed and analyzed to determine the pH of the medium being monitored.

While this invention has been described with respect to various specific examples and embodiments, it is to be understood that the invention is not limited thereto and that it can be variously practiced within the scope of the following claims.

What is claimed is:

1. A composition of matter useful in sensing the concentration of an ionic component in a medium comprising:

a first layer including a first matrix material which is solid and is permeable to the ionic component, and a sensing component in an amount effective to provide a signal which varies as the concentration of the ionic component in the medium varies; and a second layer which includes a second matrix material which is solid, is permeable to the ionic component, and is compatible with said first matrix material, and an opaque agent in an amount sufficient to render said second layer effectively opaque, said first layer and said second layer being partially intermingled to form an intermingled zone;

wherein said second layer and said intermingled zone are formed by solubilizing said second matrix material in a liquid medium, contacting said first layer with said liquid medium such that a portion of said first matrix material in said first layer is also solubilized in said liquid medium, and solidifying the solubilized first matrix material and the solubilized second matrix material such that said solidified first matrix material and a portion of said solidified second matrix material form said intermingled zone and the remainder of said solidified second matrix material forms said second layer.

2. The composition of claim 1 wherein both said first matrix material and said second matrix material are polymeric.

3. The composition of claim 1 wherein said first matrix material and said second matrix material have substantially the same chemical composition.

4. The composition of claim 1 wherein both said first matrix material and said second matrix material are cellulose.

5. The composition of claim 1 wherein both said first matrix material and said second matrix material are cellulose and said liquid medium is an aqueous basic medium.

6. The composition of claim 5 wherein said liquid medium includes a basic component selected from the group consisting of metal hydroxides, organic amines and mixtures thereof.

7. The composition of claim 1 wherein the ionic component is $H^+$ or $OH^-$.

8. The composition of claim 1 wherein said sensing component is an optical indicator.

9. The composition of claim 1 wherein said sensing component is a fluorescence indicator.

10. The composition of claim 1 wherein said sensing component is selected from the group consisting of hydroxypyrene trisulfonic acid, derivatives of hydroxypyrene trisulfonic acid, and mixtures thereof.

11. The composition of claim 1 wherein said second layer acts to substantially optically isolate at least a portion of said first layer.

12. The composition of claim 1 wherein the ratio of the thickness of the first layer to the thickness of the intermingled zone is within the range of from about 1:0.005 to about 1:0.25.

13. An apparatus useful in sensing the concentration of an ionic component in a medium comprising:

sensor means comprising a first layer which includes a first matrix material which is solid and is permeable to the ionic component and a sensing component in an amount effective to provide a signal which varies as the concentration of the ionic component in the medium varies, and a second layer which includes a second matrix material which is solid, is permeable to the ionic component, and is compatible with said first matrix material and an opaque agent in an amount sufficient to render said second layer effectively opaque, said first and second layers being partially intermingled to form an intermingled zone;

wherein said second layer and said intermingled zone are formed by solubilizing said second matrix material in a liquid medium, contacting said first layer with said liquid medium such that a portion of said first matrix material in said first layer is also solubilized in said liquid medium, and solidifying the solubilized first matrix material and the solubilized second matrix material such that said solidified first matrix material and a portion of said solidified second matrix material form said intermingled zone and the remainder of said solidified second matrix material forms said second layer; and signal means capable of transmitting said signal from said sensing component.

14. The apparatus of claim 13 wherein said sensing component is an optical indicator and said signal means comprises an optical fiber.

15. The apparatus of claim 14 wherein both said first matrix material and said second matrix material are cellulose and said liquid medium is an aqueous basic medium.

16. The apparatus of claim 15 wherein said liquid medium includes a basic component selected from the group consisting of metal hydroxides, organic amines and mixtures thereof.

17. The apparatus of claim 14 wherein said optical indicator is spaced apart from said optical fiber.

18. The apparatus of claim 13 further comprising holder means includes a cavity having an open end and being sized and adapted to receive at least a portion of said first layer, said sensor means being structured and oriented so that said first layer is located away from said open end of said cavity.

19. The apparatus of claim 18 wherein said holder means is substantially transparent, and said second layer, together with said holder means, substantially completely surrounds said first layer.

20. The apparatus of claim 13 wherein the ratio of the thickness of the first layer to the thickness of the intermingled zone is within the range of from about 1:0.005 to about 1:0.25.

21. A method for sensing the concentration of an ionic component in a medium comprising:

contacting said medium with a composition comprising a first layer including a first matrix material which is solid and is permeable to the ionic component and a sensing component in an amount effective to provide a signal which varies as the concentration of said ionic component in said medium varies, and a second layer which includes a second matrix material which is solid, is permeable to the ionic component, and is compatible with said first matrix material and an opaque agent in an amount sufficient to render said second layer effectively opaque, said first layer and said second layer being partially intermingled to form an intermingled zone;

wherein said second layer and said intermingled zone are formed by solubilizing said second matrix material in a liquid medium contacting said first layer with said liquid medium such that a portion of said first matrix material in said first layer is also solubilized in said liquid medium, and solidifying the solubilized first matrix material and the solubilized second matrix material such that said solidified first matrix material and a portion of said solidified second matrix material form said intermingled zone and the remainder of said solidified second matrix material forms said second layer;

causing said sensing component to emit a signal which varies as the concentration of said ionic component in said medium varies; and analyzing said signal to determine the concentration of said ionic component in said medium.

22. The method of claim 21 wherein said medium is blood.

23. The method of claim 21 wherein said ionic component is $H^+$ or $OH^-$.

24. The method of claim 21 wherein said both first matrix material and said second matrix material are polymeric.

25. The method of claim 21 wherein both said first matrix material and said second matrix material are cellulose.

26. The method of claim 21 wherein both said first matrix material and said second matrix material are cellulose and said liquid medium is an aqueous basic medium.

27. The method of claim 21 wherein said sensing component is selected from the group consisting of hydroxypyrene trisulfonic acid, derivatives of hydroxypyrene trisulfonic acid, and mixtures thereof, and wherein said opaque agent is carbon black.

28. The method of claim 21 wherein the ratio of the thickness of the first layer to the thickness of the intermingled zone is within the range of from about 1:0.005 to about 1:0.25.

29. A method for making a sensor useful in sensing the concentration of an ionic component in a medium comprising:

applying to a surface of a first layer of liquid composition, said first layer comprising a first matrix material which is solid prior to said applying and a sensing component in an amount effective to provide a signal which varies as the concentration of the ionic component in the medium varies, said liquid composition comprising a liquid medium, an opaque agent, and a second matrix material which is compatible with said first matrix material and which is solubilized in said liquid medium, a portion of said first matrix material from said first layer becoming solubilized in said liquid medium upon said applying; and solidifying the solubilized second matrix material and the solubilized first matrix material such that said solidified first matrix material and a portion of said solidified second matrix material form an intermingled zone and the remainder of said solidified second matrix material forms a second layer.

30. The method of claim 29 wherein both said first matrix material and said second matrix material are cellulose and said liquid medium is an aqueous basic medium.

31. The method of claim 30 wherein said aqueous basic medium includes an amine.

32. The method of claim 30 wherein said aqueous basic medium comprises water, cupric hydroxide and ethylene diamine.

33. The method of claim 29 which further comprises positioning said first layer in proximity to the optical surface of an optical fiber.

34. The method of claim 29 wherein both said first matrix material and said second matrix material are polymeric and wherein said first layer is positioned in a cavity of a sensor holder, said cavity having an open end.

35. The method of claim 29 wherein both said first matrix material and said second matrix material are cellulose.

36. The method of claim 35 wherein said solidifying step includes contacting said solubilized second matrix material and said solubilized first matrix material with an aqueous acidic medium.

37. The method of claim 29 wherein said first matrix material and said second matrix material have substantially the same chemical composition.

38. The method of claim 29 wherein the ratio of the thickness of the first layer to the thickness of the intermingled zone is within the range of from about 1:0.005 to about 1:0.25.

39. A method of making a sensor useful in sensing the concentration of an ionic component in a medium comprising:

applying to a surface of a first composition a second composition, said first composition comprising a sensing component in an amount effective to provide a signal which varies as the concentration of the ionic component in the medium varies and a first matrix material which is solid prior to said applying, said second composition comprising a liquid medium, an opaque agent, and a second matrix material which is compatible with said first matrix material and is solubilized in said liquid medium, a portion of said first matrix material from said first composition becoming solubilized in said liquid medium upon said applying, both said first matrix material and said second matrix material being cellulose, said liquid medium including a basic component selected from the group consisting of metal hydroxides, organic amines, and mixtures thereof; and solidifying the solubilized second matrix material and the solubilized first matrix material.

40. A composition of matter useful in sensing the concentration of an ionic component in a medium comprising:

a first layer including a first matrix material which is solid and is permeable to the ionic component, and a sensing component in an amount effective to provide a signal which varies as the concentration of the ionic component in the medium varies; and a second layer which includes a second matrix material which is solid, is permeable to the ionic component, and is compatible with said first matrix material, and an opaque agent in an amount sufficient to render said second layer effectively opaque, said first layer and said second layer being partially intermingled to form an intermingled zone;

wherein the ratio of the thickness of the first layer to the thickness of the intermingled zone is within the range of from about 1:0.005 to about 1:0.25.

41. The composition of claim 40 wherein the ionic component is $H^+$ or $OH^-$.

* * * * *

UNITED STATES PATENT AND TRADEMARK OFFICE
CERTIFICATE OF CORRECTION

PATENT NO. : 5,081,042

DATED : January 14, 1992

INVENTOR(S) : Masao Yafuso et al.

It is certified that error appears in the above-identified patent and that said Letters Patent is hereby corrected as shown below:

Cover page, under the heading "Inventors", "Chong" should be --Cheng--.

Line 2 of the Abstract after "component", insert --in--.

Line 7 of the Abstract, delete the comma after "material" and insert therefor a semicolon.

Col. 7, Line 68, after the first occurrence of "material" insert a comma.

Col. 11, Line 51, "includes" should be --including--.

Col. 12, Line 14, after "medium" insert a comma.

Col. 12, Line 33, in claim 24, line 1, "said both" should be --both said--.

Col. 12, Line 55, in claim 29, line 4, delete "of" and insert therefor --a--.

Col. 13, Line 38, in claim 39, line 1, "of" should be --for--.

Signed and Sealed this

Twenty-seventh Day of April, 1993

Attest:

MICHAEL K. KIRK

*Attesting Officer*  *Acting Commissioner of Patents and Trademarks*